United States Patent [19]
Sorscher et al.

[11] Patent Number: 5,552,311
[45] Date of Patent: Sep. 3, 1996

[54] PURINE NUCLEOSIDE PHOSPHORYLASE GENE THERAPY FOR HUMAN MALIGNANCY

[75] Inventors: Eric J. Sorscher; William B. Parker; Leonard L. Bennett, Jr., all of Birmingham, Ala.

[73] Assignees: University of Alabama at Birmingham Research Foundation; Southern Research Inst., both of Birmingham, Ala.

[21] Appl. No.: 122,321

[22] Filed: Sep. 14, 1993

[51] Int. Cl.$^6$ .............................. C12N 5/00; C12N 15/00
[52] U.S. Cl. ................... 435/240.2; 435/172.3; 435/252.1; 435/320.1; 424/450; 514/2; 514/43; 514/44; 530/350; 536/23.2; 536/23.7; 536/24.1; 935/70; 935/72
[58] Field of Search .................... 536/23.1, 23.5, 536/23.7, 23.2, 24.1; 530/350; 514/2.43, 44; 424/93 A, 93 B, 450; 435/172.3, 240.2, 320.1, 252.1; 935/70, 72

[56] References Cited

FOREIGN PATENT DOCUMENTS 0392745  10/1990  European Pat. Off. .
0415731   3/1991  European Pat. Off. .

OTHER PUBLICATIONS

G Kolata (Jul. 25, 1995) The New York Times p. C3.
Ram et al. *Cancer Research* 53:83–88, 1993.
Balzarini et al. *J. Biol. Chem.* 268(9):6332–6337, 1993.
Zhu et al. *Science* 261:209–211, 1993.
Culver et al. *Science* 256:1550–1552, 1992.
Mullen et al. *Proc. Natl. Acad. Sci. USA* 89:33–37, 1992.
Takamiya et al. *J. Neurosci. Resc.* 33:493–503, 1992.
McGarrity et al. *In Vitro Cell. & Dev. Biol.* 22(6):301–304, 1986.
Hooper and Subak–Sharpe *Internat'l Rev. of Cytol.* 69:45–104, 1981.
Bruce and Meeker *J. Natl. Cancer Inst.* 38(3):401–405, 1967.
H H Wellhoner et al. (1991) J Biol Chem 266:4309–4314.
Anderson, W. F., "Human Gene Therapy," *Science* 256:808–813 (1992).
Bagshawe, K. D., "Towards Generating Cytotoxic Agents at Cancer Sites." *J. Cancer* 60:275–281 (1989).
Collier, R. J., "Structure–Activity Relationships in and *Pseudomonas aeruginosa exc,*" *Immuntoxins*, A. E. Frankel, Ed. (Kluwer Academic Publishers, Boston), pp. 25–35 (1988).
Culver, K. W., et al., "Lymphocytes as Cellular Vehicles for Gene Therapy in Mouse and Man," *Science* 256:1550–1552 (1992).
Culver, K., et al., "In Vivo Gene Transfer with Retroviral Vector–Producer Cells for Treatment of Experimental Brain Tumors," *Proc. Natl. Acad. Sci. USA.* 88:3155–3159 (1991).

(List continued on next page.)

*Primary Examiner*—Bruce R. Campell
*Attorney, Agent, or Firm*—Benjamin Aaron Adler

[57] ABSTRACT

The invention provides a method of killing replicating or non-replicating, transfected or transduced mammalian cells and bystander cells, comprising the following steps: (a) transfecting or transducing mammalian cells with a nucleic acid encoding a non-human purine nucleoside phosphorylase (PNP); and (b) contacting the transfected or transduced cells with an amount of a substrate for the purine nucleoside phosphorylase sufficient to produce a toxic purine base-analog thereby killing the transfected or transduced cells and bystander cells. In the present method of killing cells, the non-human purine nucleoside phosphorylase can be an *E. coli* purine nucleoside phosphorylase. The method of the invention described above can utilize a substrate that is a purine nucleoside analog. For instance, in the method provided in the Examples, the substrate is 9-(β-D-2-deoxyerythropentofuranosyl)-6-methylpurine (MeP-dR).

14 Claims, 1 Drawing Sheet

OTHER PUBLICATIONS

Curiel, D., et al., "High–Efficiency Gene Transfer Mediated by Adenovirus Coupled to DNA–Polylsine Complexes," *Hum. Gene Ther.* 3:147–154 (1992).

Debs, R. J., et al., "Selective Enhancement of Pentamidine Uptake in the Lung by Aerosolization and Delivery in Liposomes," *Am. Rev. Respir. Dis.* 135:731–737 (1987).

Doskocil and A. Holy, "Specificity of Purine Nucleoside Phosphorylase From *Escherichia coli*," *Collection Czechoslov. Chem. Commun.* 42:370–383 (1977).

Friedmann, T., "Progress Toward Human Gene Therapy," *Science* 244:1275–1281 (1989).

Gabizon, A. and D. Papahadiopoulos, "Liposome Formulations with Prolonged Circulation Time in Blood and Enhanced Uptake by Tumors," *Proc. Natl. Acad. Sci. USA* 85:6949–6953 (1988).

Hatanka, M., et al., "Adenine Formation from Adenosine by Mycoplasmas: Adenosine Phosphorylase Activity, " *Proc. Natl. Acad. Sci. USA* 72:1401–1405 (1975).

Hershfield, M. S., et al., "Use of Site–Directed Mutagenesis to Enhance the Epitope–Shielding Effect of Covalent Modification of Proteins with Polyethylene Glycol," *Proc. Natl. Acad. Sci. USA* 88:7185–7189 (1991).

Hooper, M. L. and J. H. Subak–Sharpe, "Metabolic Cooperation between Cells," *Int. Rev. Cytol.* 69:45–104 (1981).

Houston, L. L., "Introduction," *Immunotoxins*, A. E. Frankel, Ed. (Kluwer Academic Publishers, Boston), pp. 1–7 (1988).

Huang S. K., et al., "Pharmacokinetics and Therapeutics of Sterically Stablized Liposomes in Mice Bearing C–26 Colon Carcinoma," *Cancer Research* 52:6774–6781 (1992).

Huber, B. E., et al., "Retroviral–Mediated Gene Therapy for the Treatment of Hepatocellular Carcinoma: An Innovative Approach for Cancer Therapy," *Proc. Acad. Sci. USA* 88:8039–8043 91991).

Jensen K. F. and P. Nygaard, "Purine Nucleoside Phosphorylase from *Escherichia coli* and *Salmonella typhimurium*," *Eur. J. Biochem.* 51:253–265 (1975).

Litzinger, D. C. and L. Huang, "Biodistribution and Immunotargetability of Ganglioside–Stabilized Dioleoylphosphatidylethanolamine Liposomes," *Biochimica et Biophysics Acta* 1104:179–187 (1992).

Long, C. W., et al., "Uracil Phosphoribosyl Transferase Activity of Mycoplasma and Infected Cell Cultures," *In vitro* 13:429–433 (1977).

Maruvama, K. et al., "Lipid Composition is Important for Highly Efficient Target Binding and Retention of Immunoliposomes," *Proc. Natl. Acad. Sci. USA* 87:5744–5748 (1990).

Maxwell, I. H., et al., "Regulated Expression of a Diphtheria Toxin A–Chain Gene Transfected into Human Cells: Possible Strategy for Inducing Cancer Cell Suicide," *Cancer Research* 46:4660–4664 (1986).

McGarrity, G. J. and D. A. Carson, "Adenosine Phosphorylase–Mediated Nucleoside Toxicity," *Experimental Cell Research* 139:199–206 (1982).

Miller, A. D. "Human Gene Therapy Comes of Age," *Nature* 357:455–460 (1992).

Moolten, F. L., "Tumor Chemosensitivity Conferred by Inserted Herpes Thymidine Kinase Genes: Paradigm for a Prospective Cancer Control Strategy," *Cancer Res.* 46:5276–5281 (1986).

Moolten, F. L. and J. M. Well, "Curability of Tumors Bearing Herpes Tymidine Kinase Genes Transferred by Retroviral Vectors," *J. Natl. Cancer Inst.* 82:297–300 (1990).

Murphy. J. R., "The Diphtheria Toxin Structural Gene," *Current Topics in Microbiology and Immunology* 118:235–251 (1985).

Nabel, G. J., et al., "Immunotherapy of Malignancy by In Vivo Gene Transfer into Tumors," *Hum. Gene Therapy* 3:399–410 (1992).

Parks, R. E., et al. "Purine Nucleoside Phosphorylase and 5'–Methylthioadenosine Phosphorylase: Targets of Chemotherapy," *Molecular Actions and Targets for Cancer Chemotherapeutic Agents*, (Academic Press, Inc.), pp. 229–252, 1988.

Pinnaduwage, P. and L. Huang, "Stable Target–Sensitive Immunoliposomes," *Biochemistry* 31:2850–2855 (1992).

Ram, Z., et al., "*In Situ Retroviral–Mediated Gene Transfer for the Treatment of Brain Tumors in Rats,*" *Cancer Res.* 53:83–88 (1993).

Robertus, J. D., "Toxin Structure," *Immunotoxins*, A. E. Frankel, Ed. (Kluwer Academic Publishers, Boston), pp. 11–23.

Rosenberg, S. A., et al., "Gene Transfer into Humans—Immunotherapy of Patients with Advanced Melanoma. Using Tumor Infiltrating Lymphocytes Modified by Retroviral Gene Transduction," *N. England J. Med.* 323:570–578 (1990).

Senter, P. D., "Activation of Prodrugs by Antibody–Enzyme Conjugates: A New Approach to Cancer Therapy," *FASEB J.* 4:188–193 (1990).

Senter P., et al., "Enhancement of the In Vitro and In Vivo Antitumor Activities of Phosphorylated Mitomycin C and Etoposide Derivatives by Monoclonal Antibody–Alkaline Phosphatse Conjugates," *Cancer Research* 49:5789–5792 (1989).

Senter, P. D., et al., "Anti–Tumor Effects of Antibody–Alkaline Phosphatase Conjugates in Combination with Etoposide Phosphate," *Proc. Natl. Acad. Sci. USA* 85:4842–4846 (1988).

Sorrentino, B. P., et al., "Selection of Drug–Resistant Bone Marrow Cells in Vivo After Retroviral Transfer of Human MDR1," *Science* 257 (5066);99–103 (1992).

Sorscher, E. J., et al. "Identification of a Membrane Protein from T84 Cells using Antibodies Made Against a DIDS–Binding Peptide," *Amer. J. Physiol.* 262:C136–C147 (1992).

Takamiya, Y., et al., "Gene Therapy of Malignant Brain Tumors: A Rat Glioma Line Bearing the Herpes Siplex Virus Type 1—Thymidine Kinase Gne and Wild Type Retorvirus Kills other Tumor Cells," *J. Neuroscience Res.* 33:493–503 (1992).

Tepper, R. I., et al., "Murine Interleukin–4 Displays Potent Anti–Tumor Activity in Vivo," *Cell* 57:503–513 (1989).

Thompson, L., "At Age 2, Gene Therapy Enters a Growth Phase," *Science* 358:744–746 (1992).

Trubetskov, V. S., et al., "Cationic Liposomes Enhance Targeted Delivery and Expression of Exogenous DNA Mediated by N–Terminal Modified Poly(L–lysine)–Antibody Conjugate in Mouse Lung Endothielial Cells," *Biochimica et Biophysica Acta* 1131:311–313 (1992).

Wagner, E., et al., "Transferrin–Polycation Conjugates as Carriers for DNA Uptake into Cells," *Proc. Natl. Acad, Sci. USA.* 87:3410–3414 (1990).

Wu, G. Y. and C. H. Wu, "Receptor–Mediated Gene Delivery and Expression in Vivo," *J. Biol. Chem.* 263, No.29:14621–14624 (1988).

Mullen et al., "Transfer of the bacterial gene for cytosine deaminase to mammalian cells confers lethal sensitivity to 5–fluorocytosine: A negative selection system", *Proc. Natl. Acad. Sci. (USA),* 89:33–37 (Jan. 1992).

Averett et al., "6–Methoxypurine Arabinoside as a Selective and Potent Inhibitor of Varicella–Zoster Virus", *Antimicrobial Agents and Chem.,* 35:851–857 (May 1991).

Sorcher et al., "Tumor cell bystander killing in colonic carcinoma utilizing the Escherichia coli DeoD gene to generate toxic purines", *Gene Therapy,* 1:233–238 (1994).

Parker et al., "Tumor cell bystander killing in colonic carcinoma utilizing the *E. coli* DeoD gene product to generate toxic purines", *Pro. 85th Ann. Meeting Amer. Assoc. for Cancer,* 35:374, Abstract 2229 (March 1994).

FIG.1

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GATCGCGGCC GCATGGCTAC CCCACACATT AATGCAG    37

( 2 ) INFORMATION FOR SEQ ID NO:2:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GTACGCGGCC GCTTACTCTT TATCGCCCAG CAGAACGGAT TCCAG    45

PURINE NUCLEOSIDE PHOSPHORYLASE GENE THERAPY FOR HUMAN MALIGNANCY

BACKGROUND OF THE INVENTION

Inefficiency of gene delivery, together with inadequate bystander killing represent two major conceptual hurdles in the development of a toxin-mediated gene therapy for human malignancy.

Gene transfer is rapidly becoming a useful adjunct in the development of new therapies for human malignancy. Tumor cell expression of histocompatibility antigens, cytokines, or growth factors (e.g. IL-2, IL-4, GMCSF) appears to enhance immune-mediated clearance of malignant cells in animal models, and expression of chemo-protectant gene products, such as p-glycoprotein in autologous bone marrow cells, is under study as a means of minimizing marrow toxicity following administration of otherwise lethal doses of chemotherapeutic agents (1).

Theoretically, the most direct mechanism for tumor cell killing using gene transfer is the selective expression of cytotoxic gene products within tumor cells. However, no recombinant enzyme or toxin has proven useful in mediating high levels of toxicity in unselected tumor cells. Classical enzymatic toxins such as pseudomonas exotoxin A, diphtheria toxin and ricin are unlikely to be useful in this context, since these enzymes kill only cells in which they are expressed, and no current gene transfer vector is capable of gene delivery to a sufficiently high percentage of tumor cells to make use of the above recombinant enzymes (1,2).

Another strategy that has been developed to selectively kill tumor cells involves the delivery and expression of the HSV dThd kinase gene to replicating tumor cells followed by treatment with ganciclovir (3). Ganciclovir is readily phosphorylated by the HSV dThd kinase, and its phosphorylated metabolites are toxic to the cell. Very little phosphorylation of ganciclovir occurs in normal human cells. Although only those cells expressing the HSV dThd kinase should be sensitive to ganciclovir (since its phosphorylated metabolites do not readily cross cell membranes), in vitro and in vivo experiments have shown that a greater number of tumor cells are killed by ganciclovir treatment than would be expected based on the percentage of cells containing the HSV dThd kinase gene. This unexpected result has been termed the "bystander effect" or "metabolic cooperation". It is thought that the phosphorylated metabolites of ganciclovir may be passed from one cell to another through gap junctions (3,4). However, even if a nucleoside monophosphate such as ganciclovir monophosphate were released into the medium by cell lysis, the metabolite would not be able to enter neighboring cells and would likely be degraded (inactivated) to the nucleoside by phosphatases.

Although the bystander effect has been observed in initial experiments using HSV dThd kinase, the limitations present in all current gene delivery vehicles mean that a much greater bystander effect than previously noted will be important to successfully treat human tumors using this approach. One of the difficulties with the current bystander toxicity models is that bystander toxicity with metabolites that do not readily cross the cell membrane will not be sufficient to overcome a low efficiency of gene transfer (e.g., transfection, transduction, etc.). In the known toxin gene therapy systems, the efficiency of transduction and/or transfection in vivo is generally low.

An existing protocol for treating brain tumors in humans uses retroviral delivery of HSV dThd kinase, followed by ganciclovir administration. In rat models, using HSV dThd in this context, tumor regressions have been observed (Culver et al. Science 256:1550–1552, 1992). The HSV dThd approach has not proven sufficient in humans thus far; this may in part be due to 1) inadequate bystander toxicity with HSV dThd kinase, and 2) cell killing only of dividing cells using HSV dThd kinase with ganciclovir.

Similarly, the usefulness of E. coil cytosine deaminase (which converts 5-fluorocytosine to 5-fluorouracil and could theoretically provide substantial bystander toxicity) in this regard remains to be established. Initial studies have shown that cytosine deaminase expression followed by treatment with 5-fluorocytosine in clonogenic assays leads to minimal bystander killing, (C. A., Mullen, C. A., M. Kilstrup, R. M. Blaese, Proc. Natl. Acad. Sci. USA 89:33–37 (1992)).

Prodrug activation by an otherwise non-toxic enzyme (e.g. HSV dThd kinase, cytosine deaminase) has advantages over the expression of directly toxic genes, such as ricin, diphtheria toxin, or pseudomonas exotoxin. These advantages include the capability to 1) titrate cell killing, 2) optimize therapeutic index by adjusting either levels of prodrug or of recombinant enzyme expression, and 3) interrupt toxicity by omitting administration of the prodrug (1-3,8). However, like other recombinant toxic genes, gene transfer of HSV dThd kinase followed by treatment with ganciclovir is neither designed to kill bystander cells nor likely to have broad bystander toxicity in vivo.

An additional problem with the use of the HSV dThd kinase or cytosine deaminase to create toxic metabolites in tumor cells is the fact that the agents activated by HSV dThd kinase (ganciclovir, etc.) and cytosine deaminase (5-fluorocytosine) will kill only cells that are synthesizing DNA (Balzarini et al. J. Biol. Chem. 268:6332–6337, 1993 and Bruce and Meeker J. Natl. Cancer Inst. 38:401–405, 1967). Even if a considerable number of nontransfected cells are killed, one would not expect to kill the nondividing tumor cells with these agents.

Thus, there exists a need for a toxin gene therapy method that can overcome the problems of inefficient gene delivery, cell replication-dependent killing and low toxin diffusion between cells. The present invention meets this need by providing a system that can produce cytotoxic purine bases that can freely diffuse across the cell membranes and kill both dividing and nondividing neighboring cells.

SUMMARY OF THE INVENTION

The invention provides a method of killing replicating or non-replicating, transfected or transduced mammalian cells and bystander cells, comprising the following steps: (a) transfecting or transducing mammalian cells with a nucleic acid encoding a non-human purine nucleoside phosphorylase (PNP); and (b) contacting the transfected or transduced cells with an amount of a substrate for the purine nucleoside phosphorylase sufficient to produce a toxic purine base analog thereby killing the transfected or transduced cells and bystander cells. In the present method of killing cells, the non-human purine nucleoside phosphorylase can be an E. coli purine nucleoside phosphorylase. The method of the invention described above can utilize a substrate that is a purine nucleoside analog. For instance, in the method provided in the Examples, the substrate is 9-(β-D-2-deoxyerythropentofuranosyl)-6-methylpurine (MeP-dR).

An isolated nucleic acid encoding a non-human or a genetically modified human purine nucleoside phosphorylase in mammalian cells is also provided. The invention further provides a eucaryotic transfer vector comprising a nucleic acid encoding a non-human or genetically modified human purine nucleoside phosphorylase. The vector can be in a host capable of expressing the purine nucleoside phosphorylase.

A method of treating a tumor is provided, comprising the following steps: (a) transfecting tumor cells with a nucleic acid encoding a non-human or genetically modified human purine nucleoside phosphorylase; and (b) contacting the transfected tumor cells with an amount of a substrate for the purine nucleoside phosphorylase sufficient to produce a toxic purine base analog thereby killing the transfected tumor cells and bystander cells to treat the tumor.

DETAILED DESCRIPTION OF THE INVENTION

The invention provides a method of killing replicating or non-replicating, transfected or transduced mammalian cells and bystander cells, comprising the following steps: (a) transfecting or transducing mammalian cells with a nucleic acid encoding a non-human or modified human purine nucleoside phosphorylase (PNP); and (b) contacting the transfected or transduced cells with an amount of a substrate for the purine nucleoside phosphorylase sufficient to produce a toxic purine base analog thereby killing the transfected or transduced cells and bystander cells. Thus, by delivering PNP and expressing a functional enzyme in the presence of substrate, a toxic product is produced. It should be appreciated that a "non human or modified human PNP" includes the use of both types of PNP in the same therapeutic regimen. The killing can occur in vitro or in vivo, including human therapy.

The present invention (in the embodiment exemplified below) involves transfecting cells with the *E. coil* Deo D gene (purine nucleoside phosphorylase (PNP)) and subsequently treating with a nontoxic nucleoside analog (e.g., deoxyadenosine or deoxyguanosine analogs, including N7 analogs), which is converted to a toxic purine analog. *E. coil* PNP differs from human PNP in its acceptance of adenine- and certain guanine-containing nucleoside analogs as substrates (5). *E. coli* PNP expressed in tumor cells cleaves the nucleoside, liberating a toxic purine base analog. Purine bases freely diffuse across cell membranes, whereas nucleoside monophosphates generally remain inside the cell in which they are formed. A toxic adenine analog formed after conversion by *E. coli* PNP can 1) be converted by adenine phosphoribosyl transferase to toxic nucleotides and kill all transfected cells and 2) diffuse out of the cell and kill surrounding cells that were not transfected (bystander cells).

Gene Transfer

An example of the method using gene transfection is provided in the Examples. More particularly, cationic liposome mediated transfer of a plasmid containing a non-human PNP gene is exemplified. However, other gene transfer methods will generally be applicable in the method, because the particular method for transferring the PNP gene to a cell is not determinative of successful cell killing. Thus, gene transduction, utilizing a virus-derived transfer vector, further described below, can also be used. Such methods are well known in the art and readily adaptable for use in the gene mediated toxin therapies described herein. Further, these methods can be used to target certain diseases and cell populations by using the targeting characteristics of the carrier.

The rapidly advancing field of therapeutic DNA delivery and DNA targeting also includes vehicles such as "stealth" and other antibody conjugated liposomes, (including lipid mediated drug targeting to colonic carcinoma), receptor mediated targeting of DNA through cell specific ligands, lymphocyte directed tumor targeting, and highly specific therapeutic retroviral targeting of murine glioma cells in vivo (9). It is not known whether rates of cell division within a human glioma (where tumor cell division is likely to be substantially less than in experimental brain tumor models) will support adequate levels of retrovital integration to permit tumor regression using HSV dThd kinase. The approach described here, within the context of a gene targeting mechanism either directed towards dividing tumor cells or tumor neovascularization, offers an improved means by which a small subset of tumor cells can be established within a growing tumor mass, which would mediate rapid tumor involution and necrosis after the appropriate signal, i.e. prodrug/substrate administration.

PNP Selection

In the present method of killing cells, the non-human purine nucleoside phosphorylase can be an *E. coil* purine nucleoside phosphorylase. A method using such an *E. coli* PNP is provided in the Examples. However, any PNP which can convert a substrate to produce a toxic purine base can be utilized. Thus, modifications in the *E. coil* PNP, which do not affect this activity, are within the scope of the invention. The present invention provides an example of a method by which any proposed PNP can be tested in a cell for its ability to convert a given substrate from a relatively nontoxic form to a toxin for the cells.

Substrate Selection

The method of the invention described above can utilize a substrate that is a purine nucleoside analog. For instance, in the method provided in the Examples, the substrate is 9-($\beta$-D-2-deoxyerythropentofuranosyl)-6-methylpurine (MeP-dR).

Although MeP-dR is relatively non-toxic, by defining the mechanism of its toxicity, it may be possible to further enhance the therapeutic index of this compound. For instance, if the toxicity of MeP-dR is due to phosphorylation by a deoxynucleoside kinase, then analogs that cannot be phosphorylated, such as 5'-deoxy-MeP-dR, could be synthesized and used as the prodrug to deliver MeP.

Further studies, using the methods described herein can identify other purine nucleoside analogues with a therapeutic index superior even to that shown here for MeP-dR. Expression of *E. coli* PNP (or other suitable PNP) within malignant cells can be used to screen a variety of substrates to determine which produce toxic purine bases, such as 2-fluoroadenine (substrate: 2-fluoro-2'-deoxyadenosine with 2'-deoxycytidine added to ameliorate toxicity), 2-azaadenine, 4-amino-pyrazolo [3,4-d] pyrimidine, etc. To be useful in this context, any deoxypurine nucleoside analog composed of the bases listed above, if the analog cannot be targeted to certain cell types or organs, should be a poor substrate of human enzymes (such as PNP, methylthioadenosine phosphorylase, adenosine deaminase, and nucleoside kinases), should be a good substrate for the *E. coil* or transfected other PNP, and should have low toxicity at the nucleoside level (i.e. as a prodrug or substrate). Using ribose- or deoxyribose-containing substrates, *E. coil* PNP can selectively produce a variety of toxic guanine analogs, such as 6-thioguanine or 3-deazaguanine, that are attached to ribose or deoxyribose via the N-7 position in the guanine ring (for example, D. G. Streeter et al. *Biochemical Pharmacology* 29:1791–1797 (1979)). The strategy described here for therapeutic PNP gene transfer implicates new uses for several broad classes of specifically activatable cytotoxic purines in the treatment of human malignancy. Because the growth fraction is very small in most tumors, it is preferable to select compounds that are active against both dividing and nondividing cells. It appears that some of the toxic purine analogs produced using *E. coli* PNP in the present method are toxic to nondividing as well as dividing cells. Specific examples of such purine nucleosides that will work in the present invention can be tested according to the protocols set forth in the Examples.

Target Cells

In the method of the invention described above, the mammalian cells to be killed can be tumor cells. Cells comprising any solid tumor, whether malignant or not, can be killed by the present method based on the ability to transfer or express the PNP gene selectively to at least a small percentage of cells comprising the tumor. Recently for example, it has been shown that intravenous injection of liposome carrying DNA can mediate targeted expression of genes in certain cell types. Targeting of a PNP gene or expression of the gene to a small fraction of the cells in a tumor mass followed by substrate administration could be adequate to mediate involution. (Zhu et al. *Science* 261:209–211, 1993) Through the substantial bystander effect and killing of nondividing cells demonstrated in the Examples, the present method can destroy the tumor. Although, in the exemplified method, the mammalian cells are human colonic carcinoma cells, it can be appreciated that the methods taught herein can be applied to other cells and their susceptibility to the present methods can be determined as taught.

In addition to killing tumor cells, the method of the invention can also kill virally infected cells. In a virus-killing embodiment, the gene transfer method selected would be chosen for its ability to target the expression of PNP in virally infected cells. For example, virally infected cells may utilize special viral gene sequences to regulate and permit gene expression (i.e., virus specific promoters). Such sequences are not present in uninfected cells. If *E. coil* or other PNP genes were oriented appropriately with regard to such a viral promoter, PNP would only be activated within virally infected cells, and not other, uninfected, cells. In this case, virally infected cells would be much more susceptible to the administration of MeP-dR or other substrates designed to be converted to toxic form by PNP.

Nucleic Acids

An isolated nucleic acid encoding a non-human or genetically modified human purine nucleoside phosphorylase in a mammalian cell is provided in the present invention. More specifically, the invention provides an isolated nucleic acid encoding an *E. coil* PNP in a mammalian cell. By "isolated" is meant separated from other nucleic acids found in the naturally occurring organism from which the PNP gene is obtained.

As described above, in a preferred embodiment the PNP used in the present methods can include genetically modified human or nonhuman mammalian PNP capable of reacting with a substrate that the native PNP in the cell to be killed will not recognize or recognizes very poorly. Thus, the nucleic acids of the invention that encode the PNP of the invention are present in cells in which they are not naturally found, either because they are from a different organism or because they have been modified from their natural state. The key requirement of the nucleic acids encoding the PNP is that they must encode a functional enzyme that is able to recognize and act upon a substrate that is not well recognized by the native PNP of the cell.

Vectors and Hosts

A eucaryotic transfer vector comprising a nucleic acid encoding a non-human or genetically modified purine nucleoside phosphorylase is also provided. The vector must be capable of transducing or transfecting at least some percentage of the cells to be killed. Transfer vector can be any nucleotide construction used to deliver genes into cells (e.g., a plasmid), or as part of a general strategy to deliver genes, e.g., as part of recombinant retrovirus or adenovirus (Ram et al. *Cancer Res.* 53:83–88, 1993). The Examples provide a plasmid vector containing a nucleic acid encoding an *E. coil* PNP.

The vector of the invention can be in a host capable of expressing a functional PNP. As used in the method of the invention, the host cell is the cell to be killed, which expresses the PNP and is killed by the toxic product of the reaction of the enzyme and the substrate. The host cells will be those susceptible to killing by the above method. A method of determining susceptibility is provided in the Examples which teach protocols for the transfection of host cells, and demonstrate the expression of PNP and toxicity to the host cells in the presence of substrate.

Direct Delivery of the PNP Enzyme to Cells

In addition to the present gene transfer methods, the PNP gene product can also be selectively delivered to the tumor cells by a number of different mechanisms and this PNP could be used to produce MeP at the site of the tumor.

For instance, the PNP enzyme can be attached to any desired monoclonal antibody and injected into the patient. After allowing sufficient time for the clearance of all PNP conjugated to monoclonal antibody that has not bound to the target, the patient is treated with MeP-dR, which is cleaved to MeP only at the targeted site. Such a procedure requires only the availability of an appropriate monoclonal antibody. The procedures used for conjugating proteins to target-specific monoclonal antibodies are routinely available. The following references are examples of the use of this technology to target specific proteins to tumor tissue (Senter et al. *Bioconjugate Chem.* 2:447–451, 1991; Bagshawe, K. D. *Br. J. Cancer* 60:275–281, 1989; Bagshawe et al. *Br. J. Cancer* 58:700–703, 1988; Senter et al. *Bioconjugate Chem.* 4:3–9, 1993; Battelli et al. *Cancer Immunol. Immunother.* 35:421–425, 1992; Pietersz and McKenzie *Immunolog. Reviews* 129:57–80, 1992; and Roffler et al. *Biochem. Pharmacol* 42:2062–2065, 1991. Other ligands, in addition to monoclonal antibodies, can be selected for their specificity for a target cell and tested according to the methods taught herein.

It is also possible to entrap proteins in liposomes and target them to specific tissues. The PNP gene product can, thus, be selectively delivered to a tumor mass using targeted liposomes. After all non-targeted liposome is cleared from the blood, the patient is treated with MeP-dR which is cleaved to MeP by the PNP only at the targeted site. Once again, this procedure requires only the availability of an appropriate targeting vehicle. The following references are examples of the use of this technology to target specific proteins to tumor tissue (Hughes et al. *Cancer Research* 49:6214–62210, 1989; and Litzinger and Huang *Biochimica et Biophysica Acta* 1104:179–187, 1992).

Treatment Methods

A method of treating a tumor is provided, comprising the following steps: (a) transfecting or transducing tumor cells with a nucleic acid encoding a non-human or genetically modified human purine nucleoside phosphorylase; and (b) contacting the transfected tumor cells with an amount of a substrate for the purine nucleoside phosphorylase sufficient to produce a toxic purine base analog thereby killing the transfected tumor cells and bystander cells to treat the tumor. The non-human purine nucleoside phosphorylase can be *E. coli* purine nucleoside phosphorylase. Alternatively, other PNP can be used as described herein. The substrate can be a deoxyadenosine analog, such as 9-(β-D-2-deoxyerythropentofuranosyl)-6-methylpurine as illustrated in the Examples. Alternatively, other purine nucleosides, as described herein can be used.

The invention provides a method of treating a tumor by killing replicating and non-replicating, targeted mammalian cells and bystander cells, comprising the following steps: 1) delivering a non-human or modified human PNP enzyme to the targeted mammalian cells; and 2) contacting the targeted cells with an amount of a substrate for the purine nucleoside phosphorylase sufficient to produce a toxic purine base analog thereby killing the targeted cells and bystander cells. The method can provide PNP enzyme to cells using monoclonal antibodies or other target cell-specific ligands or by using liposomes as described above.

The amount of substrate effective to produce a toxic compound in the presence of PNP should be an amount less than an amount that is toxic to the subject. For example, using the formula of Freireich et al. (*Cancer Chemother. Rep.* 50:219–244, 1966) the maximum tolerated dose for a human subject is determined. Based on systemically administered dose response data in mice showing that a dose of 25 mg (MeP-dR) per kg per day for 9 days (9 doses total) resulted in some toxicity, but no lethality, a human dosage of 75 mg MeP-dR/m$^2$ was determined according to the formula: 25 mg/kg×3=75 mg/m$^2$. This amount or slightly less should result in maximal effectiveness of tumor cell killing without killing the subject. This standard of effectiveness is accepted in the field of cancer therapy. However, more preferred is a range of from about 10% to 1% of the maximum tolerated dosage (e.g., 7.5 mg/m$^2$–0.75 mg/m$^2$). Furthermore, it is understood that modes of administration that permit the substrate to remain localized at or near the site of the tumor will be effective at lower doses than systemically administered substrates.

The substrate may be administered orally, parenterally (e.g., intravenously), by intramuscular injection, by intraperitoneal injection, transdermally, or the like. The exact amount of substrate required will vary from subject to subject, depending on the species, age, weight and general condition of the subject, the severity of the disease that is being treated, the location and size of the tumor, the particular compound used, its mode of administration, and the like. Thus, it is not possible to specify an exact amount. However, an appropriate amount may be determined by one of ordinary skill in the art using only routine experimentation given the teachings herein. Generally, dosage will preferably be in the range of about 0.5–50 mg/m$^2$.

Depending on the intended mode of administration, the substrate can be in pharmaceutical compositions in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected substrate in combination with a pharmaceutically acceptable carrier and, in addition, may include other medicinal agents, pharmaceutical agents, carriers, diluents, etc. By "pharmaceutically acceptable" is meant a material that is not biologically or otherwise undesirable, i.e., the material may be administered to an individual along with the selected substrate without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences* (Martin, E. W. (ed.) latest edition Mack Publishing Co., Easton, Pa.).

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Treatment Kit

A kit comprising the vector of the invention and a substrate for the purine nucleoside phosphorylase is provided.

PNP can be exploited as part of a general strategy for titratable, tumor specific cell killing. In addition, because colonic carcinoma is highly refractory to all known conventional modalities of chemotherapy and radiotherapy, the present invention provides a gene transfer method that represents a useful adjunct in toxin mediated tumor cell killing, even in otherwise resistant human malignancies.

The following examples are intended to illustrate, but not limit, the invention. While the protocols described are typical of those that might be used, other procedures known to those skilled in the art may be alternatively employed.

EXAMPLES

Effect of MeP-dR on Human Colon Carcinoma Cells Expressing E. coli PNP

Substrate

MeP-dR was chosen because it is 20-fold less toxic than 6-methylpurine (MeP) to HEp-2 cells and it has been used to detect cultures infected with mycoplasma, because mycoplasma express an enzyme similar in function to *E. coli* PNP (J. A. Montgomery, and K. Hewson, *J. Med. Chem.* 11:48–52 (1968). G. J. McGarrity, and D. A. Carson, *Experimental Cell Research* 139:199–206 (1982); M. Hatanka, R. Del Guidice, C. Long, *Proc. Natl. Acad. Sci. USA* 72:1401–1405 (1975), C. W. Long, R. Del Guidice, R. S. Gardella, M. Hatanka, In vitro 13:429–433 (1977)).

Cell lines

T84 cells (E. J. Sorscher, et al. *Amer. J. Physiol.* 262:C136–C147 (1992)) were grown in Dulbecco's modified eagle medium containing F12 nutrient medium (DMEM/F12) (Gibco) (BRL) in 6 well trays to a density of approximately $1-2 \times 10^5$ cells/well (~20% confluency).

Toxicity of MeP-dR within colon carcinoma cells

Untransfected T-84 were treated with increasing concentrations of either MeP-dR or MeP. After 5 days the cells were removed from each well and the number of dye excluding cells were determined with the aid of a hemacytometer. Cells were studied both at passage 48 (p.48) and passage 61 (p.61). MeP was obtained from Sigma Chemical Company. MeP-dR was synthesized as described (J. A. Montgomery, and K. Hewson, *J. Med. Chem.* 11:48–52 (1968)). The nucleoside and base were dissolved in serum free DMEM/F12 at a concentration of 1 mg/ml and added directly to 1 ml DMEM/F12 with 10% fetal bovine serum at the concentrations described below in order to cover $1-2 \times 10^5$ cells/well.

Initial cytopathic effects due to MeP were observed within 24 hours (e.g. rounding of cells, with some cells detaching from plate). Viable cells were counted 5 days following addition of drug. The higher concentrations (3.75 μm–75 μm) of MeP resulted in cell lysis and complete loss of cellular architecture, leaving only cellular debris within wells by day 2 following treatment; trypan blue exclusion was used to confirm viability in cells retaining recognizable structure at all concentrations studied. At lower concentrations MeP-dR did not cause any appreciable cell death and higher concentrations (200 and 400 μM) less than half of the cells were killed. If the toxicity of MeP-dR is due to very low levels of liberation of MeP by human PNP, then combination with selective inhibitors of human PNP could prevent this toxicity (J. A. Montgomery, et al. *J. Medicinal Chem.* 36:55–69 (1993)).

Enhanced Toxicity of MeP-dR Mediated by E. coil PNP Expression

Plasmids

*E. coli* (strain JM101) chromosomal DNA template was obtained using the method described in (N. J. Gay, J. Bacteriol. 158:820–825 (1984)). Two PCR primers gATCgCggCCgCATggCTACCCCACACATTAATgCAg (SEQ' ID NO:i) and gTACgCggCCgCTTACTCTT-TATCgCCCAgCAgAACggATTCCAg (SEQ ID NO:2) were used to define the full length coding sequence of the *E. coli* DeoD gene (5) and to incorporate Not 1 sites at both 5') and 3' ends of the desired product. After 30 cycles of amplification ($94° \times 1$ min denaturation, $50° \times 2$ min annealing, and $72° \times 3$ min elongation using 1 ng template, 100 ng of each primer in a 100 μl reaction mixture containing 2.5 units taq polymerase, 200 μm each dNTP, 50 mM KCl, 10 mM Tris Cl (pH 8.3), 1.5 mMMg $Cl_2$ and 0.01% gelatin (weight/vol), a single PCR product of the predicted size (716 base pairs) was obtained. This product was extracted with phenol/chloroform, precipitated with ethanol, digested with Not I, and gel purified using the Gene Clean kit, (Bio. 101, La Jolla, Calif.).

In order to obtain a vector capable of directing eukaryotic expression of *E. coli* PNP, the Lac Z gene was excised from pSVβ (Clontech, Palo Alto, Calif.) by digestion with Not I, the vector backbone was dephosphorylated (calf intestinal alkaline phosphatase, GIBCO BRL, Gaithersburg, Md.) and gel purified as above. The PNP insert, prepared as above, was then ligated into the Not I ends of the plasmid backbone in order to create a new construct with PNP expression controlled by the SV-40 early promoter. Correct recombinants (and orientation of inserts) were confirmed by restriction mapping (using 12 restriction digests/plasmid with enzymes which cut in both vector and insert), and by reamplification of the full length insert from recombinant plasmid using the primers described above.

Transfection

Cationic liposome mediated gene transfer was used to transfect T84 cells. Briefly, 6μg of plasmid containing PNP or Lac Z was added to 10μg of a 1:1 molar mixture of DOTMA/DOPE (lipofectin (GIBCO BRL, Gaithersburg, Md.)) in a final volume of 200 μl DMEM/F12 serum free medium. After a 10 minute incubation at room temperature, the DNA lipid mixture was added to 500μL serum free medium and was used to cover the cells within a well. Four hours later, transfection medium was removed from each well and 2 ml DMEM/F12 with 10% fetal bovine serum was added.

Transfection efficiency

The Lac Z gene was transfected into T-84 cells as described above. Briefly, using a lipid mediated genes transfer protocol identical to that described above, 6μg of plasmid containing the *E. coli* Lac Z genes under the control of the SV-40 early promoter was transferred into $1-2 \times 10^5$ T84 cells. 48 hours after transfection, cells were washed 3 times in PBS, fixed at 4° C.×10 minutes in 0.2% glutaraldehyde, (in 80 mM $NaHPO_4$), rinsed 2 times with PBS, and then stained in a solution containing 80 mM $Na_2HPO_4$, 20 mM $NaH_2PO_4$, 1.3 mM MgCl, 3 mM $K_3Fe(CN)_6$, 3 mM $K_4Fe(CN)_6$ and 1 mg/ml X-gal (5-bromo-4-chloro-3-indolyl-β-D-galactopyranoside). 12 hours after staining, 0.1–1% of the cells treated with β-galactosidase DNA stained positive for gene expression.

X-gal staining of these cells two days after transfection indicated an overall transfection efficiency of 0.1–1% (as determined by percentage of blue cells). No positive cells were observed in untreated T84 cells, in cells treated with lipid alone, or plasmid DNA alone. Similar conclusions were reached using a Lac Z reporter gene containing a nuclear targeting sequence and leading to nuclear staining of recombinant cells.

Addition of MeP-dR 48 hours following transfection, fresh medium was added and MeP-dR (1mg/ml in PBS) was added directly to the cells to achieve the desired final concentrations. Cell viability was measured 5 days following treatment as described above for the MeP-dR toxicity study.

Figure 1:
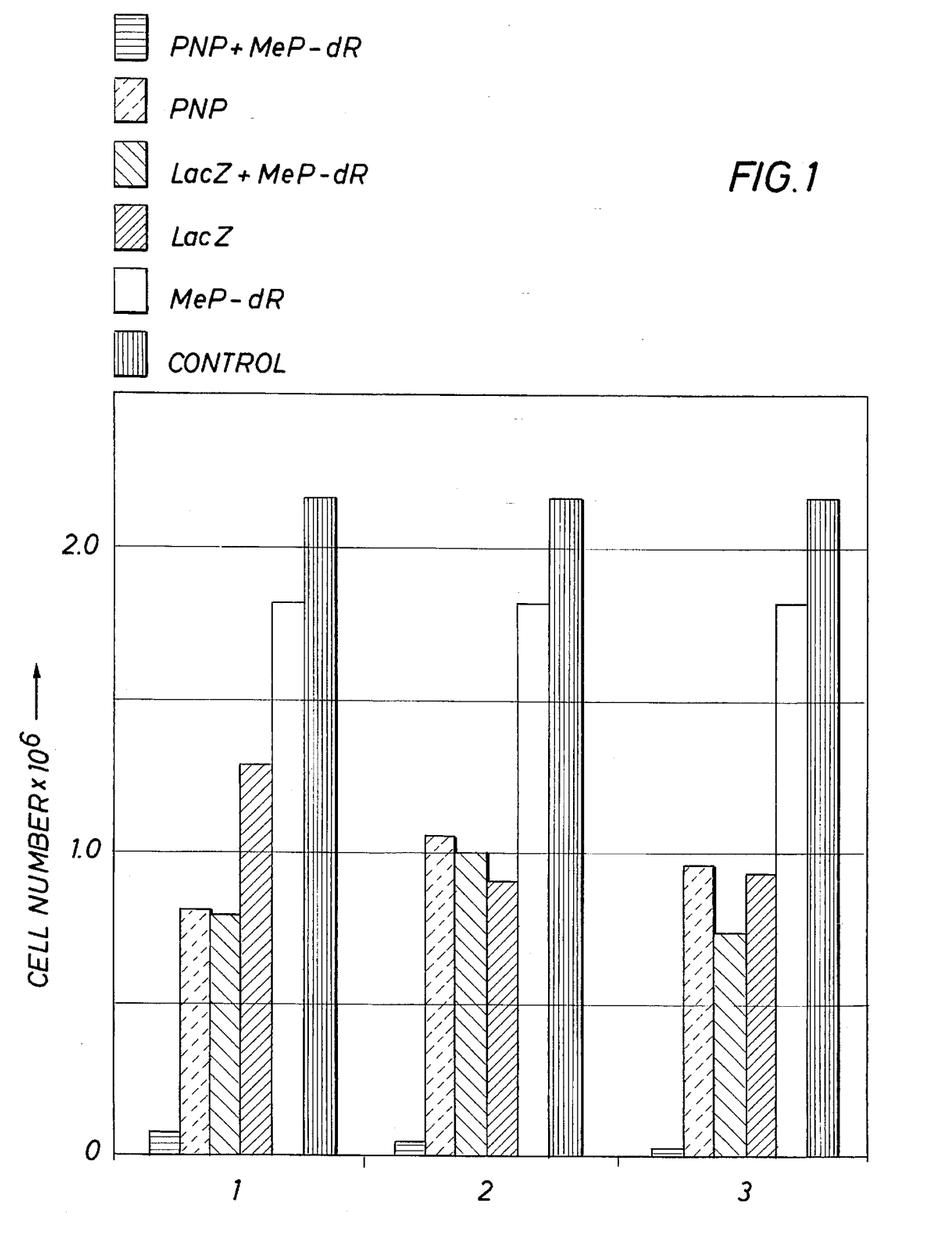
FIG. 1 shows the effect of MeP-dR on control cells and on cells transfected with cDNA encoding either lacZ or *E. coli* purine nucleoside phosphorylase.

In one experiment, MeP-dR (160 μM) was added to wells containing untransfected cells, or cells transfected with 10, 20, or 40μg (1, 2, and 3 of FIG. 1, respectively) of cDNA containing either the E. coil PNP or Lac Z genes under control of the SV-40 early promoter (in otherwise comparable vector contexts). After 5 days the cells were removed from each well and the number of dye excluding cells were determined with the aid of a hemacytometer. 30–50% toxicity due to the DOTMA. DOPE (transfection) protocol is acceptable for cationic liposome mediated gene transfer to T84 in vitro when performed under optimal conditions. The results of this study are shown in FIG. 1.

In an additional experiment, approximately $2 \times 10^5$ cells per well were transfected as above using 6 μg of plasmid containing E. coil PNP cDNA. Two days after transfection, varying concentrations of MeP-dR (0, 2, 4, 20, 40 and 160 μM were added to the wells, and after 5 days the dye excluding cells were counted with the aid of a hemacytometer. Concentrations of MeP-dR as low as 4 μM resulted in greater than 80% inhibition of cell growth.

An experiment was also performed in triplicate in which $2 \times 10^5$ cells per well were transfected with Lac Z or PNP using the protocol described for transfection. Two days after transfection, 16μM MeP-dR was added to one set of the cultures transfected with PNP and one set of the cultures transfected with Lac Z. The other PNP and Lac Z transfected cultures did not receive drug. The results demonstrate minimal cell killing in all cultures except the PNP-transfected, MeP-dR treated culture.

In the above experiments, MeP-dR (160 μM) was minimally toxic to the cells that were not transfected. While expression of the Lac Z gene had no influence on toxicity mediated by MeP-dR, MeP-dR killed virtually all of the cells transfected with the E. coil PNP (FIG. 1). Substantial killing could also be seen with 16 μM MeP-dR after PNP transfection. These results indicate that low efficiency expression of E. coil PNP cDNA (expression in less than 1% of tumor cells) was adequate for nearly 100% transfected cell and bystander cell killing. In addition, because diffusion of MeP into the medium covering the cells could have a substantial dilutional effect, it may be that an even lower fraction of tumor cells expressing E. coil PNP in vivo might be able to mediate tumor cell necrosis in the presence of MeP-dR.

Activity of E. coil PNP on MeP-dR in Cell Extracts

In order to confirm that the toxicity of MeP-dR in T84 cells expressing the E. coil PNP gene was due to its conversion to MeP, E. coil PNP activity was measured in transfected T84 cells. Briefly, T84 cells transfected with 6 μg of plasmid containing either the E. coil PNP gene or the β-galactosidase gene as described above (see transfection) were collected by centrifugation 48 hours after transfection and resuspended in 3 volumes of 0.01M potassium phosphate (pH 7.4) followed by incubation on ice for 15 minutes. The pellet was homogenized, and the sample was centrifuged at 100,000×g for 60 minutes. PNP activity was measured in 100 μl volumes containing 50 mM potassium phosphate (pH 7.4), 100 μM of MeP-dR, and 1 mg/ml of protein from the cell extract. After incubation for 24 hours at 25° C., the reaction was stopped by boiling, the precipitated proteins were removed by centrifugation, and the reaction mixture was subjected to HPLC by injection onto a Spherisorb ODS1 (5 μm) column (Keystone Scientific Inc., State College, Pa.). The MeP-dR and MeP were eluted with a 30 min isocratic gradient of 50 mM ammonium dihydrogen phosphate buffer (pH 4.5)/acetonitrile (95/5; v/v) at a flow rate of 1 ml/min. MeP-dR and MeP were detected by their absorbance at 261 nm.

Approximately 24% of the MeP-dR was converted to MeP in extracts from cells transfected with the E. coil PNP, whereas no conversion occurred in cell extracts from colon carcinoma cells transfected with the Lac Z gene. Total PNP activity measured using inosine as substrate was not changed in T84 cells transfected with E. coil PNP.

Detection of MeP in medium of TS4 cells transfected with E. coil PNP

MeP-dR (160 μM) was added 48 hours after transfection of T84 cells with the E. coil PNP gene. Five days after the addition of MeP-dR the medium was collected, and the proteins were precipitated by boiling. After centrifugation, the medium was analyzed for the appearance of MeP by reverse phase HPLC as described above.

MeP was detected in the culture medium of T84 cells transfected with E. coil PNP. More than 75% of the MeP-dR was converted to MeP over a 5 day period. These results have significance, since they indicate that 1) untransfected and mock transfected colonic carcinoma cells lack the enzymatic mechanism for conversion of MeP-dR to MeP, 2) as predicted, MeP was readily released into the extracellular medium, so as to establish effective bystander killing, and 3) the extracellular concentrations of MeP generated by recombinant PNP were sufficient to fully explain the bystander killing which was observed. In addition, these results establish that SV-40 driven expression of the prokaryotic PNP in eukaryotic cells (as with the E. coil Lac Z) leads to a highly active and functional enzyme. Because E. coil PNP is believed to assemble as a homohexamer in prokaryotic cells, the mechanisms of E. coil PNP oligomerization are likely to be compatible with eukaryotic protein synthesis.

Toxicity to Nondividing Cells

Results from two experiments indicate that MeP is able to kill non-proliferating cells. This distinguishes MeP from most other currently used anti-tumor agents.

In the first experiment, CEM cells were cultured in 1% serum instead of the normal 10% serum for 48 hours. Under these conditions, the cells stop growing and the cell numbers stabilize at 1.5 to 2 times the original cell numbers. Cell growth continues when cells are returned to culture medium containing 10% serum. Addition of MeP at a final concentration of 10 μg/ml to CEM cell cultures after 48 hours of incubation with 1% serum caused a decline in cell numbers to approximately 25% of their original number, which indicated that MeP was toxic to non-proliferating cells.

In the second experiment, the effect of MeP on the incorporation of thymidine into DNA, uridine into RNA, and leucine into protein was determined. RNA and protein synthesis were affected most by treatment with MeP. Effects on DNA synthesis occurred only after effects on RNA and protein synthesis were evident. These results indicated that the inhibitory effect of MeP on either RNA or protein synthesis was responsible for its toxicity. These two functions are vital to all cells regardless of their proliferative state, which indicates that MeP should be toxic to both proliferating and non-proliferating cells.

Human Treatment with Liposome Delivery

The E. coil PNP gene can also be used as part of a strategy to treat metastatic solid tumors, such as with melanoma, pancreatic, liver or colonic carcinoma. No effective therapy for metastatic tumors of these types currently exists. In this method, plasmid DNA containing a PNP gene under the control of tumor specific promoters is used. For example, the tyrosinase promoter is highly specific for mediating expression in melanoma tumor cells, and will not lead to gene expression in other tissue types (Vile and Hart Cancer Res. 55:962–967, 1993). The PNP gene under the regulatory control of this promoter, therefore, should be activated predominantly within a melanoma tumor and not elsewhere within a patient. Promoters specific for other tumor types (e.g. promoters active in the rapidly dividing endothelial cells present in all solid tumors such as the tie gene promoter in neovascular cells) can be used to specifically activate PNP only within a primary or metastatic tumor. In this method, plasmid DNA containing PNP under the control of a tumor specific promoter can be administered systemically in a complex with cationic liposomes. For example, based on animal studies, 100–400 mg plasmid DNA complexed to 1200–3600 micromoles of a 1:1 mixture of the lipids DOTMA (1,2,-dioleyloxypropyl-3-trimethyl ammononium bromide) and DOPE (dioleoyl phosphatidylethanolamine) can be used to deliver the PNP gene to tumor metastases in patients. Substrate in the above described amounts can then be administered as described above.

Human Treatment with Retrovirus Delivery

The PNP gene can be used to activate prodrugs in the treatment of human brain cancer (Recombinant Advisory Committee of the National Institutes of Health, Protocol #9206-019, Oldfield et al., approval date 6-1-92). In this method, a cell line producing retrovital particles (in which the viral particles contain the E. coil PNP gene) is injected into a CNS tumor within a patient. An MRI scanner is used to appropriately target the retroviral producer cell line to within the tumor mass. Because the retrovirus is only fully active within dividing cells and most of the dividing cells within the cranium of a cancer patient are within the tumor, the retrovirus is primarily active in the tumor itself, rather than in non-malignant cells within the brain. Clinical features of the patient including tumor size and localization, determine the amount of producer cells to be injected. For example, a volume of producer cells in the range of 30 injections of 100 microliters each (total volume 3 ml with approximately 1×10$^8$ producer cells/ml injected) are given under stereotactic guidance for surgically inaccessible tumors. For tumors which can be approached intraoperatively, 100 microliter aliquots are again injected (at ~1×10$^8$ cells/ml) with total injected volumes up to 10 milliliters. The present invention, using E. coil PNP gene transfer, followed by MeP-dR administration permits both bystander killing and toxicity to non-dividing cells with a greater likelihood of tumor involution than previous attempts using HSV dThd and ganciclovir.

Alternative Substrate Selection 2-fluoro-2'-deoxyadenosine (2-F-2'-deoxyadenosine) was cleaved to 2-F-adenine to the same degree as inosine by a crude extract of E. coil cells, which suggested that 2-F-2'-deoxyadenosine was a substrate for the E. coil PNP. No 2-F-adenine was produced when 2-F-2'-deoxyadenosine was incubated with purified human PNP. 2-F-2'-deoxyadenosine is toxic to human cells due to its phosphorylation to F-dATP. The metabolism and toxicity of 2-F-2'-deoxyadenosine can be prevented by incubation in the presence of 2'-deoxycytidine. In in vitro cell cytotoxicity studies, 2-F-adenine is at least 50-fold more toxic to human cells than 2-F-2'-deoxyadenosine plus deoxycytidine. These results indicate that 2-fluoro-2'-deoxyadenosine plus deoxycytidine can be used to treat tumors containing the E. coil PNP. Liberation of 2-F-adenine in transfected or virally transduced tumor cells would diffuse to neighboring cells that did not contain the E. coil PNP and would kill them. This testing protocol can be used to assess other substrates for suitability in the present methods.

Throughout this application various publications are referenced by citation or numbers within parentheses. The disclosures of these publications in their entireties are hereby incorporated by reference into this application in order to more fully describe the state of the art to which this invention pertains. Full citations for these publications are as follows:

REFERENCES

1. W. F. Anderson, Science 256:808–813 (1992); A. D. Miller, Nature 357:455–460 (1992); T. Friedmann, Science 244:1275–1281 (1989); L. Thompson, Science 358:744–746 (1992); R. I. Tepper, P. K. Pattengale, P. Leder, Cell 57:503–513 (1989); G. J. Nabel, A. et al., Hum. Gene Therapy 3:399–410 (1992); B. P. Sorrentino, et al., Science 257 (5066):99–103 (1992).
2. L. L. Houston, IN: Immunotoxins, A. E. Frankel, Ed. (Kluwer Academic Publishers, Boston), pp. 1–7 (1988); J. D. Robertus, ibid. pp. 11–23; R. J. Collier, ibid. pp. 25–35 (1988); J. R. Murphy, Current Topics in Microbiology and Immunology 118:235–251 (1985); I. H. Maxwell, F. Maxwell, L. M. Glode, Cancer Research 46:4660–4664 (1986); K. D. Bagshawe, J. Cancer 60:275–281 (1989 ).
3. Z. Ram, K. W. Culver, S. Walbridge, R. M. Blaese, E. H. Oldfield, Cancer Res. 53:83–88 (1993); F. L. Moolten, Cancer Res. 46:5276–5281 (1986); F. L. Moolten, and J. M. Wells, J. Natl. Cancer. Inst. 82:297–300 (1990); B. E. Huber, C. A. Richards, T. A. Krenitsky, Proc. Acad. Sci. U.S.A. 88:8039–8043 (1991); Y. Takamiya, et al., J. Neuroscience Res. 33:493–503 (1992); K. W. Culver et al., Science 256:1550–1552 (1992).
4. M. L. Hooper, and J. H. Subak-Sharpe, Int. Rev. Cytol. 69:45–104 (1981).
5. K. F. Jensen and P. Nygaard, Eur. J. Biochem. 51:253–265 (1975); J. Doskocil and A. Holy, Collection Czechoslov. Chem. Commun. 42:370–383 (1977); R. E. Parks, et al. (Purine Nucleoside Phosphorylase) IN: Molecular Actions and Targets for Cancer Chemotherapeutic Agents, (Academic Press, Inc.), pp. 229–252, 1988; M. S.

Hershfield et al. *Proc. Natl. Acad. Sci. U.S.A.* 88:7185–7189 (1991).

6. E. J. Sorscher, et al. *Amer. J. Physiol.* 262-:C136–C147 (1992).

7. G. J. McGarrity, and D. A. Carson, *Experimental Cell Research* 139:199–206 (1982); M. Hatanka, R. Del Guidice, C. Long, *Proc. Natl. Acad. Sci. U.S.A.* 72:1401–1405 (1975), C. W. Long, R. Del Guidice, R. S. Gardella, M. Hatanka, *In vitro* 13:429–433 (1977).

8. P. D. Senter, *FASEB J.* 4:188–193 (1990); P. D. Senter et al., *Cancer Research* 49:5789–5792 (1989); P. D. Senter et al., *Proc. Natl. Acad. Sci. U.S.A.* 85:4842–4846 (1988).

9. S. K. Huang et al., *Cancer Research* 52:6774–6781 (1992); R. J. Debs et al., *Am. Rev. Respir. Dis.* 135:731–737 (1987); K. Maruyama, S. J. Kennel, L. Huang, *Proc. Natl. Acad. Sci. U.S.A.* 87:5744–5748 (1990); P. Pinnaduwage, and L. Huang, *Biochemistry* 31:2850–2855 (1992); A. Gabizon, and D. Papahadjopoulos, *Proc. Natl. Acad. Sci. U.S.A.* 85:6949–6953 (1988); S. A. Rosenberg, et al., *N. England J. Med.* 323:570–578 (1990); K. Culver et al., Proc. Natl. Acad. Sci. U.S.A.. 88:3155–3159 (1991); G. Y. Wu, and C. H. Wu, *J. Biol. Chem.* 263, No.29:14621–14624 (1988); E. Wagner, M. Zenke, M. Cotten, H. Beug, and M. L. Birnstiel, *Proc. Natl. Acad, Sci. U.S.A..* 87:3410–3414 (1990); D. T. Curiel et al., *Hum. Gene Ther.* 3:147–154 (1992); D. C. Litzinger, and L. Huang, *Biochimica et Biophysica Acta* 1104:179–187 (1992); V. S. Trubetskoy, V. P. Torchilin, S. Kennel, L. Huang, *Biochimica et Biophysica Acta* 1131:311–313 (1992).

transfected or transduced cultured mammalian cells and bystander cells, comprising:

(a) transfecting or transducing mammalian cells with a nucleic acid encoding an *E. coli* purine nucleoside phosphorylase, whereby the purine nucleoside phosphorylase is expressed and (b) contacting the transfected or transduced cells with an effective amount of a nucleoside substrate for the purine nucleoside phosphorylase, wherein the substrate is non-toxic to mammalian cells and is cleaved by the phosphorylase to yield a putinc base which is toxic to the targeted mammalian cells and bystander cells, to kill the mammalian cells expressing the phosphorylase and the bystander cells.

2. The method of claim 1 wherein the substrate is a 9-(β-D-2-deoxyerythropentofuranosyl)-6-methylpurine.

3. The method of claim 1, wherein the cells are tumor cells.

4. The method of claim 1, wherein the cells are virally infected cells.

5. The method of claim 1, wherein the mammalian cells are human colonic carcinoma cells.

6. A method of killing replicating or non-replicating, targeted cultured mammalian cells and bystander cells, comprising the following steps:

(a) delivering an *E. coli* putinc nucleoside phophorylase to the targeted mammalian cells; and (b) contacting the targeted cells with an effective amount of a nucleoside substrate for the putinc nucleoside phosphorylase, wherein the substrate is non-toxic to mammalian cells and is cleaved by the phosphorylase

---

---

What is claimed is:

1. A method of killing replicating or non-replicating, to yield a putinc base which is toxic to the targeted mammalian cells and bystander cells, to kill the mammalian cells expressing the phosphorylase and the bystander cells.

7. The method of claim 6, wherein the substrate is a deoxyadenosine nucleoside analog.

8. The method of claim 6, wherein the substrate is 9-(β-D-2-deoxyerythropentofuranosyl)-6-methylpurine.

9. The method of claim 6, further comprising coupling the purine nucleoside phosphorylase to a molecule specifically binding to the target cell.

10. A vector comprising a DNA sequence coding for an *E. coli* purine nucleoside phosphorylase protein and said vector is capable of replication in a host which comprises, in operable linkage:

a) an origin of replication;

b) a promoter functional in a mammalian cell; and c) a DNA sequence coding for said protein.

11. The vector of claim 10, wherein said vector is selected from the group consisting of a retroviral vector, an adenoviral vector, an adeno-associated virus vector and a plasmid.

12. A host cell transfected with the vector of claim 10, said vector expressing an *E. coil* purine nucleoside phosphorylase protein.

13. The host cell of claim 12, wherein said cell is selected from the group consisting of bacterial cells, mammalian cells and insect cells.

14. A liposome containing an *E. coil* purine nucleoside phosphorylase protein.

* * * * *